US009041935B2

(12) United States Patent
Yao et al.

(10) Patent No.: US 9,041,935 B2
(45) Date of Patent: May 26, 2015

(54) MEASURING POLARIZATION CROSSTALK IN OPTICAL BIREFRINGENT MATERIALS AND DEVICES BASED ON REDUCTION OF LINE BROADENING CAUSED BY BIREFRINGENT DISPERSION

(75) Inventors: Xiaotian Steve Yao, Diamond Bar, CA (US); Xiaojun Chen, San Gabriel, CA (US)

(73) Assignee: General Photonics Corporation, Chino, CA (US)

( * ) Notice: Subject to any disclaimer, the term of this patent is extended or adjusted under 35 U.S.C. 154(b) by 0 days.

(21) Appl. No.: 13/482,813

(22) Filed: May 29, 2012

(65) Prior Publication Data
US 2013/0321818 A1 Dec. 5, 2013

(51) Int. Cl.
G01B 9/02 (2006.01)
G01N 21/00 (2006.01)
G01J 4/00 (2006.01)
G01J 4/02 (2006.01)
G01N 21/23 (2006.01)

(52) U.S. Cl.
CPC .. *G01J 4/02* (2013.01); *G01N 21/23* (2013.01)

(58) Field of Classification Search
CPC .................................. G01N 21/23; G01J 4/02
USPC ......................................... 356/73.1, 477, 491
See application file for complete search history.

(56) References Cited

U.S. PATENT DOCUMENTS

| 5,064,270 | A | 11/1991 | Turpin et al. |
| 5,206,924 | A * | 4/1993 | Kersey ............................ 385/24 |
| 5,712,704 | A * | 1/1998 | Martin et al. .................. 356/491 |
| 7,227,645 | B2 | 6/2007 | Cyr |
| 7,920,253 | B2 | 4/2011 | Cyr et al. |
| 2006/0081772 | A1* | 4/2006 | Williams et al. .......... 250/227.14 |
| 2010/0231911 | A1* | 9/2010 | Fischer et al. ................ 356/364 |
| 2011/0277552 | A1 | 11/2011 | Chen et al. |

OTHER PUBLICATIONS

Tang et al. "Distributed measurement of birefringence dispersion in polarization-maintaining fibers" Optics Letters Bo. 31, No. 23, Dec. 1, 2006.*
Fercher et al. "Numerical dispersion compensation for Partial Coherence Interferometry and Optical Coherence Tomography", Optics Express, vol. 9, No. 12, Dec. 3, 2001.*
Li, et al. "Method for improving the resolution and accuracy against birefringence dispersion in distributed polarization cross-talk measurements" Jul. 1, 2012, Optics Letters, vol. 38, No. 13.*
Cyr, N., et al., "Random-scrambling tunable Potdr for distributed measurement of cumulative PMD," Journal of Lightwave Technology, 27(18):4164-4174, Sep. 2009.
Ding, Z., et al., "Accurate method for measuring the thermal coefficient of group birefringence of polarization-maintaining fibers," Optics Letters, 36(11):2173-2175, Jun. 2011.
Ding, Z., et al., "Improving the quality of polarization-maintaining fiber coils using distributed polarization crosstalk testing," Journal of Optoelectronics. Laser. 21(3), 430-434, Mar. 2010.

(Continued)

*Primary Examiner* — Kara E Geisel
*Assistant Examiner* — Dominic J Bologna
(74) *Attorney, Agent, or Firm* — Perkins Coie LLP

(57) ABSTRACT

Techniques and devices for measuring polarization crosstalk in birefringence optical media including polarization maintaining fiber.

18 Claims, 7 Drawing Sheets

(56) References Cited

OTHER PUBLICATIONS

Faustini, L., et al., "Bend loss in single-mode fibers," Journal of Lightwave Technology, 15(4):671-679, Apr. 1997.

Flavin, D.A., et al., "Dispersion of birefringence and differential group delay in polarization-maintaining fiber," Optics Letters, 27(12):1010-1012, Jun. 2002.

Francois, P.L, et al., "Three ways to implement interfacial techniques: application to measurements of chromatic dispersion, birefringence, and nonlinear susceptibilities," Journal of Lightwave Technology, 7(3):500-513, Mar. 1989.

Gardner, W.B., et al., "Microbending loss in optical fibers," the Bell System Technical Journal, 54(2):457-465 Feb. 1975.

Hlubina, P., et al., "Dispersion of group and phase modal birefringence in elliptical-core fiber measured by white-light spectral interferometry," Optics Express, 11(22):2793-2798, Nov. 2003.

Li, M.J., et al., "Ultra-low bending loss single-mode fiber for FTTH," Journal of Lightwave Technology, 27(3):376-382, Feb. 2009.

Martin, P., et al., "Test apparatus of distributed polarization coupling in fiber gyro coils using white light interferometry," Proc. SPIE, Fiber Optic Gyros: 15th Anniversary Conf, vol. 1585, pp. 173-179, Sep. 1991.

Saida, T., et al., "Distributed fiber-optic stress sensor by synthesis of the optical coherence function," IEEE Photonics Technology Letters, 9(4):484-486, Apr. 1997.

Shibata, N., et al., "Interference between two orthogonally polarized modes traversing a highly birefringent air-silica microstructure fiber," Journal of Lightwave Technology, 23(3):1244-1252, Mar. 2005.

Shibata, N., et al., "Temporal coherence properties of a dispersively propagating beam in a fiber-optic interferometer," Journal of the Optical Society of America a: Optics, Image Science, and Vision, 4(3):494-497, Mar. 1987.

Shlyagin, M., et al., "Birefringence dispersion measurement in optical fibers by wavelength scanning," Optics Letters, 20(8):869-871, Apr. 1995.

Sunnerud, H., et al., "Measurement of polarization mode dispersion accumulation along installed optical fibers," IEEE Photonics Technology Letters, 11(7):860-862, Jul. 1999.

Takada, K., et al., "Measurement of spatial distribution of mode coupling in birefringent polarization-maintaining fiber with new detection scheme," Optics Letters, 11(10):680-682, Oct. 1986.

Tang, F., et al., "Characterization of birefringence dispersion in polarization-maintaining fibers by use of white-light interferometry," Applied Optics, 46(19):4073-4080, Jul. 2007.

Ulrich, R., et al., "Bending-induced birefringence in single-mode fibers," Optics Letters, 5(6):273-275, Jun. 1980.

Wang, Q., et al, "Theoretical and experimental investigations of macro-bend losses for standard single mode fibers," Optics Express, 13(12):4476-4484, Jun. 2005.

Zendenhnam, A., et al., "Investigation of bending loss in a single-mode optical fiber," PRAMANA—Journal of Physics, 74(4):591-603, Apr. 2010.

\* cited by examiner

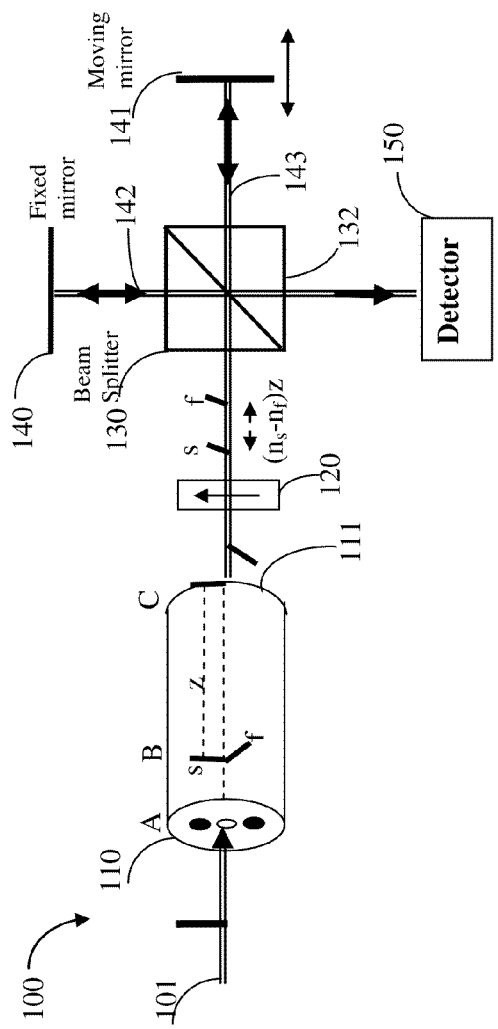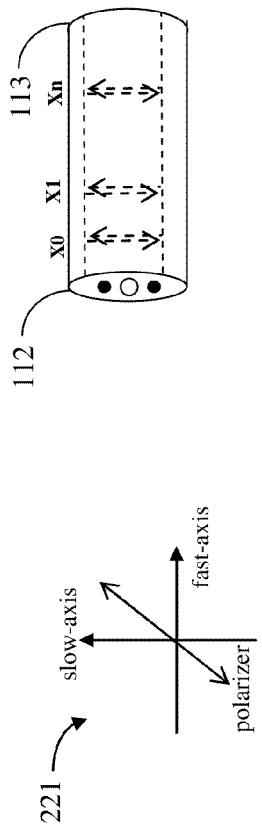
Fig. 1A
Fig. 1C
Fig. 1B
FIG. 1

MEASURING POLARIZATION CROSSTALK IN OPTICAL BIREFRINGENT MATERIALS AND DEVICES BASED ON REDUCTION OF LINE BROADENING CAUSED BY BIREFRINGENT DISPERSION

BACKGROUND

This patent document relates to devices, systems and techniques for measuring optical polarization property in optical materials and devices.

Optical polarization is an important parameter of an optical signal in various optical devices, systems and applications. The optical polarization of an optical signal can change or be altered by interacting with an optical medium having optical birefringence in which light experiences different refractive indices at different optical polarizations. Fibers, for example, may be optically birefringent and light propagating in such fibers can change its polarization. The birefringence of a fiber may change with time, often randomly with the fluctuations in the operating conditions such as stresses or temperatures in the fiber.

Polarization maintaining (PM) fiber is an example of an optical birefringent material and exhibits high birefringence and supports two discrete polarization modes, $HE^{Slow}_{11}$ and $HE^{fast}_{11}$, that are along mutually orthogonal slow and fast axes of the PM fiber. The refractive index of the PM fiber for light polarized along the slow axis in the mode $HE^{Slow}_{11}$ is higher than the refractive index of the PM fiber for light polarized along the fast axis in the mode $HE^{fast}_{11}$. When the light coupled into the PM fiber is linearly polarized along the slow axis of the PM fiber, only $HE^{Slow}_{11}$ mode is excited and the optical polarization of the guided light is maintained along the slow axis; conversely, when the light coupled into the PM fiber is linearly polarized along the fast axis of the PM fiber, only $HE^{fast}_{11}$ mode is excited and the optical polarization of the guided light is maintained along the fast axis. This characteristics of preserving optical polarization in the PM fiber can be used in various applications, such as fiber optic gyroscopes, integrated optics devices, high-performance interferometer and Polari metric sensors, quantum key distribution, and fiber lasers. Perturbations to PM fiber, such as stresses exerted on PM fiber, may cause optical coupling or crosstalk between the two orthogonal polarization modes where optical energy of one polarization mode transfers to optical energy of another polarization mode or vice versa.

SUMMARY

This document includes techniques and devices for measuring polarization crosstalk in birefringence optical birefringent media including polarization maintaining fiber.

In one aspect, a method for measuring polarization crosstalk in an optical birefringent medium is provided to include coupling a linearly polarized light of a broadband spectrum into an optical birefringent medium that supports two orthogonal polarization modes due to optical birefringence to produce an optical output signal out of the optical birefringent medium; directing the optical output signal into an optical interferometer to obtain optical interference of light between the two orthogonal polarization modes; processing the obtained optical interference to obtain an envelope spectral function of a polarization crosstalk between the two orthogonal polarization modes in the optical birefringent medium; and applying a compensation function based on measurements of the optical birefringent medium to the envelope spectral function to reduce a spectral broadening in the envelope spectral function caused by optical birefringent dispersion in the optical birefringent medium.

One implementation of the above method includes using spectral widths of the envelope spectral function measured at two or more different locations along the optical path in the optical birefringent medium to extract the optical birefringent dispersion of the optical birefringent medium; and using the obtained birefringent dispersion in the optical birefringent medium to generate the compensation function for correcting spectral broadening caused by the optical birefringent dispersion in the optical birefringent medium. In this regard, the method may be implemented to further include applying the compensation function to the envelope spectral function by multiplying the envelope spectral function by the compensation function to produce a modified envelope spectral function that has a spectral width with reduced spectral broadening caused by the optical birefringent dispersion.

The above and other aspects and their implementations area described in detail in the description, the drawings and the claims.

BRIEF DESCRIPTION OF DRAWINGS

FIG. 1 shows an exemplary device for measuring spatial distribution of polarization crosstalk in an optical birefringent medium (e.g., a PM fiber) by using an optical interferometer, where FIG. 1A shows the components of the device, FIG. 1B illustrates the orientation of the optical polarizer with respect to optical axes of the PM fiber and FIG. 1C illustrates a situation where stresses are present at multiple locations along the PM fiber to induce cross talk between the two orthogonal polarization modes of the PM fiber.

DETAILED DESCRIPTION

Figure 2:
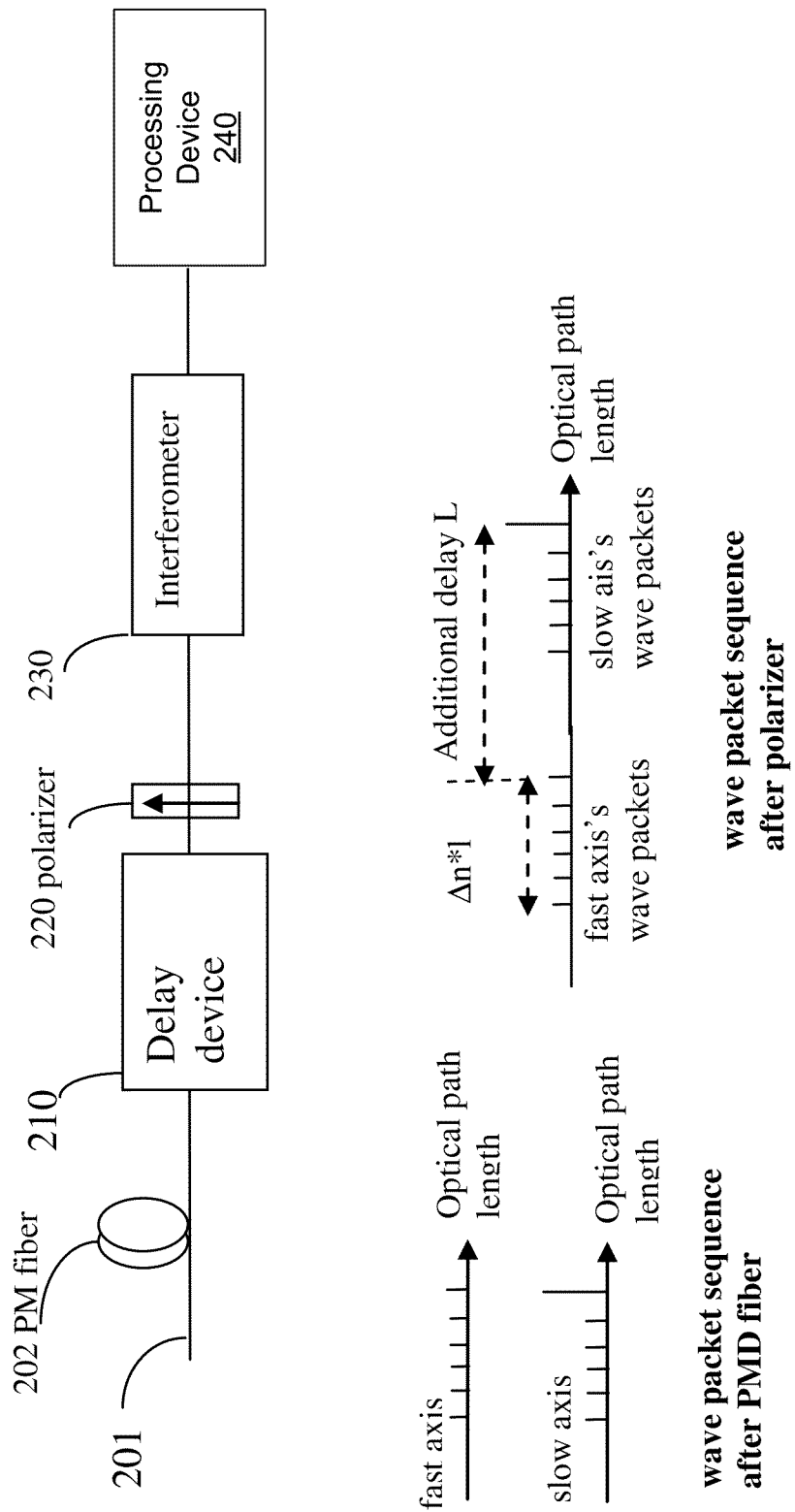
FIG. 2 shows an exemplary device for measuring polarization crosstalk in an optical birefringent medium (e.g., a PM fiber) by providing an optical delay device between the PM fiber under test and the optical interferometer, where inserts further illustrate operation of the device.

Examples for implementing techniques and devices in measuring polarization crosstalk between two polarization modes in an optical birefringent medium are provided based on optical interferometric measurements of PM fiber. The described techniques and devices can be used to effectively suppress undesired spectral broadening caused by optical birefringent dispersion in the PM fiber. Broadband light can be used in the described techniques and devices to obtain spatially resolved distribution of stresses along the PM fiber by analyzing stress-induced polarization cross-coupling along the length of the PM fiber. High measurement sensitivity, a wide dynamic range, and high spatial measurement accuracy can be achieved by using the described techniques and devices.

In a PM fiber, when the launched light is perfectly aligned along slow or fast axis at the input of the PM fiber, the optical coupling between the two polarization modes in the PM fiber occurs because intrinsic defects exist in the PM fiber or/and external stresses exerted on the PM fiber. The mode coupling between the slow axis and fast axis of the PM fiber can be characterized with polarization crosstalk. One way to represent the polarization crosstalk is the light intensity ratio between the light in the two polarization modes with optical polarizations along the slow and fast axes, respectively. In practical applications, it is desirable to identify the position of the polarization crosstalk in the PM fiber and to measure the degree of the polarization crosstalk. For example, in fiber optic gyroscopes application, the polarization crosstalk measurements can be used to screen the PM fiber before winding PM coil and to control crosstalk degradation during coil winding and to diagnose the PM coil problem after winding. The PM fiber can be used as an optical sensing medium and the polarization crosstalk can be used as a sensing mechanism. For example, the polarization crosstalk measurements can be used to obtain the stress distribution along the PM fiber and monitor space-resolved structural changes along bridges, tunnels, dams, pipeline or pipes for transporting a liquid (e.g., oil) or a gas (e.g., natural gas), or buildings. The polarization crosstalk measurements can also be used to detect an intrusion to a PM fiber link because mechanical disturbances to the PM fiber introduced by the intrusion causes polarization coupling in the PM fiber. The polarization crosstalk measurements can be used for PM fiber quality inspection by identifying defective sections of PM fiber where the crosstalk occurs, enabling the manufacturers or users to remove the defective fiber sections or take preventive measures to mitigate the impact of such defects. The polarization crosstalk measurements can also be used for measuring high polarization extinction ratios of a polarizing waveguide, obtaining the autocorrelation function of a light source, measuring the birefringence of a PM fiber and the lengths of PM fibers and single-mode (SM) fibers, and matching the optical path lengths of an interferometer.

Optical interference between light waves along the slow and fast axes of the PM fiber can generate real optical interference signals generated at the cross coupling locations in the PM fiber and ghost interference signals caused by the multiple coupling of light wave among multiple crosstalk points. The ghost signals can be strong when there are several strong coupling points on PM fiber, and thus result in wrong identification of crosstalk position and amplitude.

FIG. 1 shows an exemplary device 100 for measuring spatial distribution of polarization crosstalk along a PM fiber by using an optical interferometer, where FIG. 1A shows components of the device, FIG. 1B illustrates the orientation of the optical polarizer with respect to optical axes of the PM fiber and FIG. 1C illustrates a situation where stresses are present at multiple locations along the PM fiber to induce cross talk between the two orthogonal polarization modes of the PM fiber.

In this example, a broadband light (101) from a broadband light source is directed into the PM fiber at position A (110). The light (101) has one polarization component aligned to the slow axis of the PM fiber. Stress at position B induces polarization coupling between the two orthogonal polarizations along the fast and slow axes of the PM fiber and produces a polarization component aligned to the fast axis. Because the two polarization components travel at different group velocities in the PM fiber, the two polarization components experience a delay difference at the output (111) of the fiber (position C):

$$\Delta z = n_s z - n_f z = \Delta n z \qquad (1)$$

where $n_s$ and $n_f$ are the refractive indices of the slow and fast axes, respectively, the difference between the two refractive indices $\Delta n$ is the birefringence, and z is the distance between the coupling point B and the output point C. If an optical polarizer (120) with its optical polarization axis oriented at 45 degrees from the slow axis (FIG. 1B) is placed after the fiber output (111), one half of the optical power in each of the two polarization components passes through the polarizer (120) and emerges with the same polarization state which is linear, aligned to the polarizer axis of the polarizer (120).

Therefore, when an optical interferometer is used to receive the output light from the polarizer (120), the presence of the polarizer (120) can cause the received light, which includes two polarization components that are respectively in the two polarization modes in the PM fiber, to optically interfere. This optical interference can then be used to perform the polarization crosstalk measurements.

In FIG. 1, a Michelson interferometer is shown as an example for implementing the optical interferometer. A beam splitter 130 is provided to receive the output light from the polarizer 120 and splits the received light into a first beam along a first optical path 142 to a fixed mirror 140 and a second beam along a second optical path 143 to a movable mirror 141. An actuator is engaged to the movable mirror 141 to move the position of the movable mirror 141 to adjust the optical path length of the second optical path 143 relative to the first optical path 142. The two mirrors 140 and 144 reflect the two beams back to retrace the first and second optical paths to reach the beam splitter 130. The reflected beams from the two mirrors 140 and 141 spatially overlap with each other at the beam splitter 130 and optically interfere to produce the optical output 132 which contains the optical interference signal which has periodic interference peaks as the mirror 141 is moved in position. The distance associated with the movement of the mirror 141 between the two adjacent interference peaks in the optical interference signal is $\Delta n z$ and, accordingly, from Eq. (1), the location of the coupling point in the PM fiber is $z = \Delta z / \Delta n$. The coupling point can therefore be located using the interference graph. The coupling ratio can also be calculated from the strength of the interference peaks.

FIG. 1C illustrates presence of multiple coupling points in the PM fiber. Under this condition, the measurement process is more complicated. Assuming there are (n+1) coupling points $(x_0\ x_1\ x_2\ \ldots\ x_n)$ in the PM fiber, a linearly-polarized input wave packet (112) along the slow axis splits to $2^n$ small wave packets along the slow axis and $2^n$ small wave packets along the fast axis at the output end of PM fiber (113). Therefore, after the ith coupling point, the two wave packets sequences $P_{si}$ and $P_{fi}$ polarized along the slow axis and fast axis respectively include $2^i$ wave packets in each sequence and their optical paths length can be described as $$P_{s_i} = \begin{pmatrix} P_{s_i,1} \\ P_{s_i,2} \\ \vdots \\ P_{s_i,j} \\ \vdots \\ P_{s_i,2^i} \end{pmatrix} \quad (2)$$

$$P_{f_i} = \begin{pmatrix} P_{f_i,1} \\ P_{f_i,1} \\ \vdots \\ P_{f_i,j} \\ \vdots \\ P_{f_i,2^i} \end{pmatrix}$$

where $P_{s_i,j}$ (j=1 to $2^i$) and $P_{f_i,j}$ (j=1 to $2^i$) represent the optical patch lengths of the jth wave packet in sequences $P_{si}$ and $P_{fi}$, respectively. The optical path length of the wave packet sequences after the (i+1)th coupling point can be calculated by $$P_{s_{i+1}} = P_{f_{i+1}} = \begin{pmatrix} (x_{i+1} - x_i)n_s + P_{s_i 1} \\ (x_{i+1} - x_i)n_s + P_{s_i 2} \\ \vdots \\ (x_{i+1} - x_i)n_s + P_{s_i,2^i} \\ (x_{i+1} - x_i)n_f + P_{f_i 1} \\ (x_{i+1} - x_i)n_f + P_{f_i 2} \\ \vdots \\ (x_{i+1} - x_i)n_f + P_{f_i,2^i} \end{pmatrix}, \quad (3)$$

Based on formula (3), the optical path length of the wave packet at output of PM fiber can be obtained by $$P_{sn} = P_{fn} \quad (4)$$

$$= \begin{pmatrix} (x_n - x_{n-1})n_s + Ps_{n-1,1} \\ (x_n - x_{n-1})n_s + Ps_{n-1;2} \\ \vdots \\ (x_n - x_{n-1})n_s + Ps_{s_{i-1},2^{n-1}} \\ (x_n - x_{n-1})n_f + Pf_{n-1;1} \\ (x_n - x_{n-1})n_f + Pf_{n-1;2} \\ \vdots \\ (x_n - x_{n-1})n_f + Pf_{n-1,2^{n-1}} \end{pmatrix}$$

$$= \begin{pmatrix} (x_n - x_0)n_s \\ (x_n - x_{n-1})n_s + Ps_{n-1,2} \\ \vdots \\ (x_i - x_{n-1})n_s + Ps_{n-1,2^{n-1}} \\ (x_n - x_{n-1})n_f + Pf_{n-1;1} \\ (x_n - x_{n-1})n_f + Pf_{n-1,2} \\ \vdots \\ (x_n - x_{n-1})n_f + Pf_{n-1,2^{n-1}-1} \\ (x_n - x_0)n_f \end{pmatrix}$$

and the corresponding intensity $I_{sn}$ and $I_{fn}$ of wave packet sequences $P_{sn}$ and $P_{fn}$ can be calculated by the following formulae:

$$Is_n = \frac{Is_{n-1}}{1+c_n} \oplus \frac{c_n}{1+c_n} If_{n-1} \quad (5)$$

$$= \begin{pmatrix} Is_{n-1,1}/(1+c_n) \\ Is_{n-1,2}/(1+c_n) \\ Is_{n-1,3}/(1+c_n) \\ \vdots \\ Is_{n-1,2^{i-1}}/(1+c_n) \\ If_{n-1,1} * c_n/(1+c_n) \\ If_{n-1,2} * c_n/(1+c_n) \\ If_{n-1,3} * c_n/(1+c_n) \\ \vdots \\ If_{n-1,2^{n-1}} * c_n/(1+c_n) \end{pmatrix}$$

$$\approx \begin{pmatrix} Is_{n-1,1}/(1+c_n) \\ Is_{n-1,2}/(1+c_n) \\ Is_{n-1,3}/(1+c_n) \\ \vdots \\ Is_{n-1,2^{i-1}}/(1+c_n) \\ 0 \\ 0 \\ 0 \\ \vdots \\ 0 \end{pmatrix}$$

$$If_n = \frac{c_n}{1+c_n} Is_{n-1} \oplus \frac{1}{1+c_n} If_{n-1} \quad (6)$$

$$= \begin{pmatrix} Is_{n-1,1} * c_n/(1+c_n) \\ Is_{n-1,2} * c_n/(1+c_n) \\ Is_{n-1,3} * c_n/(1+c_n) \\ \vdots \\ Is_{n-1,2^{i-1}} * c_n/(1+c_n) \\ If_{n-1,1}/(1+c_n) \\ If_{n-1,2}/(1+c_n) \\ If_{n-1,3}/(1+c_n) \\ \vdots \\ If_{n-1,2^{n-1}}/(1+c_n) \end{pmatrix}$$

$$\approx \begin{pmatrix} 0 \\ 0 \\ 0 \\ \vdots \\ 0 \\ If_{n-1,1}/(1+c_n) \\ If_{n-1,2}/(1+c_n) \\ If_{n-1,3}/(1+c_n) \\ \vdots \\ If_{n-1,2^{n-1}}/(1+c_n) \end{pmatrix}$$

where $c_n$ is the coupling coefficients at point xn, and can be used to represent a crosstalk parameter defined by Crosstalk=abs(10*log $c_n$).

After passing through the 45° aligned polarizer (120), the two wave packet sequences $P_{sn}$ and $P_{fn}$, originally polarized along the slow axis and fast axis in the PM fiber, will be the mixed into one wave packet sequence polarized along transmission direction of the polarizer (120). The optical path length P and the corresponding optical intensity of the wave packet sequence polarized along transmission direction of the polarizer (120) can be calculated as $$P = \begin{pmatrix} p1 \\ p2 \\ p3 \\ \vdots \\ p_{2^n} \end{pmatrix} = \begin{pmatrix} (x_n - x_{n-1})n_s \\ (x_n - x_{n-1})n_s + Ps_{n-1,2} \\ \vdots \\ (x_n - x_{n-1})n_s + Ps_{n-1,2^{n-1}} \\ \hline (x_n - x_{n-1})n_f + Pf_{n-1;1} \\ (x_n - x_{n-1})n_f + Pf_{n-1,2} \\ \vdots \\ (x_n - x_{n-1})n_f + Pf_{n-1,2^{n-1}-1} \\ (x_n - x_0)n_f \end{pmatrix} = \begin{pmatrix} Ps_{n-1} \\ Pf_{n-1} \end{pmatrix} \quad (7)$$

$$I \approx \begin{pmatrix} Is_{n-1,1}/(1+c_n) \\ Is_{n-1,2}/(1+c_n) \\ Is_{n-1,3}/(1+c_n) \\ \vdots \\ Is_{n-1,2^{i-1}}/(1+c_n) \\ \hline If_{n-1,1}/(1+c_n) \\ If_{n-1,3}/(1+c_n) \\ If_{n-1,3}/(1+c_n) \\ \vdots \\ If_{n-1,2^{n-1}}/(1+c_n) \end{pmatrix} = \begin{pmatrix} Is_{n-1} \\ If_{n-1} \end{pmatrix} \quad (8)$$

As the mirror 141 moves to change its position in the second optical path, any two pulses in wave packet sequence P (see formula 7) can generate an interference signal and the position of interference pattern is determined by the delay difference between these two pulses. There are total $2^n*(2^n-1)/2$ peaks that are generated in which there are n interference peaks representing the actual coupling points and the rest of the interference peaks are ghosts peaks. These ghost peaks not only generate fake coupling signals, but also can possibly produce compositions at the true interference peaks associated with the true coupling locations. Therefore, the presence of the ghost peaks degrades the measurement accuracy in measuring the crosstalk distribution and amplitude.

Formulae (7) and (8) show that, the wave packet sequence has two groups, one represented by the top half of Formula (7) and comes from $Psn_{-1}$ polarized along the slow-axis when in the PM fiber, and another is represented by the bottom half of Formula (7) and comes from $Pf_{n-1}$ polarized along the fast axis when in the PM fiber. The positions of interference patterns between any two pulses in the group $Ps_{n-1}$ have nothing to do with the length of the last PM segment $(x_n - x_{n-1})$, and their delay difference are all shorter than the $(x_{n-1} - x0)*\Delta n$. The positions of interference patterns between any two pulses in the group $Pf_{n-1}$ also has nothing to do with the length of last PM segment $(x_n - x_{n-1})$, and their delay difference are all less than the $(x_{n-1} - x0)*\Delta n$. For the interference between top and bottom half of wave packet P, the delay difference between any one wave packets from group of $Ps_{n-1}$ and $Pf_{n-1}$, respectively, is $(x_n - x_{n-1})\Delta n + (Ps_{n-1,j} - Pf_{n-1,k})$. If the length of the last PM segment $x_n - x_{n-1}$ is longer than the length of the total length $(x_{n-1} - x_0)$ of the PM segments from 0 to n−1, the interference peaks will split into two groups at position. One group is generated by the interference between any two wave packets in sequence $Ps_{n-1}$ or $P_{sf-1}$; another group is generated by the interference between one wave packet in sequence $Ps_{n-1}$ and one in $P_{sf-1}$ respectively. A high value for the extinction ratio (ER) of a PM fiber link generally suggests that the coupling coefficients of c1, c2 . . . ci in the PM fiber link are very small so the pulse P1 in formula (7) has a relatively high power. If the wave packets generated by over two times coupling and over three order's interference are ignored, there are only n interference signals in the second interference group and the corresponding delay difference between the first optical path 142 as the reference arm of the optical interferometer (in FIG. 1A) and the second optical path 143 as the changing arm of the optical interferometer are:

$$(x_n - x_{n-1})\Delta n + \begin{pmatrix} 0 \\ (x_{n-1} - x_{n-2})\Delta n \\ (x_{n-1} - x_{n-3})\Delta n \\ \vdots \\ (x_{n-1} - x_0)\Delta n \end{pmatrix} \quad (9)$$

which corresponds to the coupling points from 0 to n−1 at the PM fiber.

To reduce the ghost interference peaks, an optical delay can be inserted between the PM fiber and the polarizer (212) to selectively cause an additional delay in light in one of the two polarization modes of the PM fiber. FIG. 2 shows an exemplary device for measuring spatial distribution of polarization crosstalk along a PM fiber by providing an optical delay device between the PM fiber under test and the optical interferometer, where inserts further illustrate operation of the device. The input light (201) is split to two orthogonal sequences wave packets after passing though the PM fiber under test (202) and the two sequences are polarized along the slow-axis and the fast-axis of the PM fiber, respectively. The delay device 210 adds an additional delay L between these two orthogonal wave packet sequences, and the delay L in vacuum should be longer than $\Delta n*l$ where $\Delta n$ is the birefringence of the PM fiber and l is the length of the PM fiber and the additional delay L is added to the light polarized along the slow axis of the PM fiber in this example. After passing the 45 degree aligned polarizer (220), these two sequences of wave packets with the additional delay L are mixed together with the same polarization state defined by the polarizer (220). An optical interferometer 230 is provided downstream from the polarizer (22) to produce a serial of interference signals at delays between $\Delta n*l$ and $(L-\Delta n*l)$, these interference signals only correspond the real signals caused by polarization coupling at coupling locations and ghosts peaks are suppressed or eliminated. A processing device 240 is provided to receive the output of the optical interferometer 230 and processes the data in the output to generate the measurements for the locations of coupling points in the PM fiber and the magnitudes of the coupling at the respective coupling points.

Consider a situation where there are three coupling points x1, x2 and x3 along the PM fiber and the light input to the PM fiber has no fast axis component and is polarized along the slow axis of the PM fiber. At each coupling point, light is coupled not only from the polarization mode along the slow axis to the polarization mode along the fast axis, but also from the polarization mode along the fast axis to the polarization mode along the slow axis. As a result of this coupling, the resulted wave packet series output by the PM fiber include wave packets caused by multiple couplings.

After passing through the 45° oriented analyzer, the wave packets aligned to the slow and fast axes will be mixed together. If this mixed light is input to an interferometer, a series of interference peaks can be observed as the delay in one arm of the interferometer is changed. Generated interference peaks represent both actual coupling points in the PM fiber and ghost peaks which do not correspond to actual coupling points in the PM fiber and thus can undesirably cause errors in identification of the actual coupling points. Ghost peaks can also be superimposed on the real peaks, reducing the crosstalk measurement accuracy.

In order to suppress the number and magnitude of the undesired ghost peaks, the delay device 210 in FIG. 2 can be inserted between the PM fiber's output and the polarizer's input. This delay device is polarization selective and can add an additional delay between the slow axis and the fast axis of the PM fiber. Thus, the two wave packet sequences from the fast-axis and slow-axis are separated in time after the light passes through the analyzer. If we preset the same delay offset between the fixed and moving arms in the interferometer, the zero order, second order and most higher order interference signals will not be generated as the delay line scans; therefore, most of the ghost peaks disappear during measurement. Consequently, the device in FIG. 2 has higher position measurement accuracy, higher dynamic range and higher sensitivity than other interferometer-based devices such as the device in FIG. 1.

The polarization-selective optical delay device (210) in FIG. 2 can be implemented in various configurations and can be selected based on the needs of a particular application for the device (210) in FIG. 2. Light in the two polarization modes of the PM fiber can be separated into two optical signals along two separate paths by using a polarization beam splitter and a variable optical delay mechanism can be used to cause a variable optical delay between the two separated optical signals before recombining the two separated signals into a combined optical signal for subsequent processing by the downstream linear optical polarizer and the optical interferometer. These examples can be configured as fixed optical delay devices that produce a desired optical delay $\Delta L$ ($>\Delta n*l$ where l is the length of PM fiber under test) or a variable delay that can be controlled to be at the above desired optical delay $\Delta L$. The ghost peaks can be suppressed by using the proper delay as shown in FIG. 2 as described in U.S. Patent Publication No. US 2011/0277552 A1 under U.S. patent application Ser. No. 12/780,593 entitled "Measuring distributed polarization crosstalk in polarization maintaining bier and optical birefringent material" and filed on May 14, 2010, which is incorporated by reference as part of the disclosure of this document.

Space-resolved polarization cross-talk measurements along a polarization maintaining (PM) fiber have various applications, including distributed stress sensing, fiber gyro coil inspection, PM fiber birefringence and beat length measurement, polarization cross-talk location identification in a PM fiber interferometer system, and PM fiber quality inspection. Scanning Michelson white light interferometers can be used to obtain such distributed polarization cross-talk measurements. Unfortunately, as the length of the fiber under test (FUT) increases, the measured cross-talk peaks will be broadened due to birefringence dispersion, resulting in reduced spatial resolution and degraded cross-talk measurement accuracies for PM fibers with a length exceeding certain lengths, e.g., a few hundred meters.

The techniques provided here can be used for improving the resolution and accuracy of distributed polarization crosstalk measurements in a polarization maintaining (PM) fiber against its birefringence dispersion. In some implementations, the broadening of measured polarization cross-talk peaks caused by birefringence dispersion can be restored by simply multiplying the measurement data with a compensation function. The birefringence dispersion variable in the function can be obtained by finding the widths of measured cross-talk envelops at known distances along the fiber. This technique can effectively improve spatial resolution and amplitude accuracy of the space-resolved polarization crosstalk measurements of long PM fibers.

Figure 3:
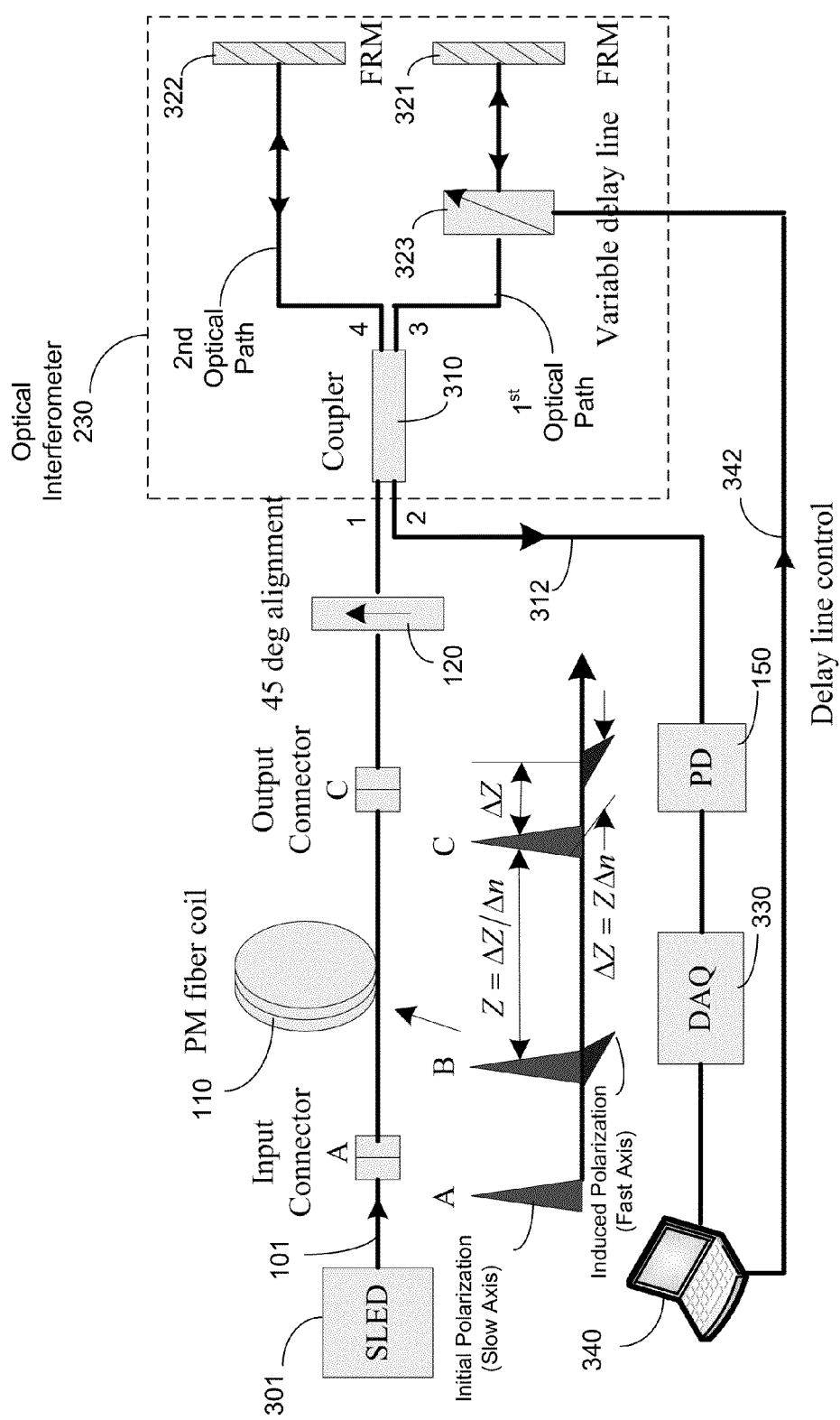
FIG. 3 shows an example device for measuring polarization crosstalk in an optical birefringent medium based on applying a birefringent dispersion compensation function.

In the following sections, implementations details are provided for mathematically compensating the birefringence dispersion in polarization cross-talk measurements of a PM fiber to improve the spatial resolution and measurement accuracy. An example of the compensation function is derived to demonstrate that the effect of birefringence dispersion on polarization-cross-talk measurements can be compensated mathematically. An exemplary white light interferometer based distributed polarization cross-talk analyzer is described. This device was used to measure the initial space-resolved polarization cross-talk peaks along the PM fiber and the spectral widths of the cross-talk peaks as a function of their location along the fiber to obtain the birefringence dispersion $\Delta D$ for the dispersion compensation function. In addition, numerical multiplication of the compensation function with the original measured cross-talk data is performed to eliminate the dispersion induced broadening of the cross-talk peaks. Experiments conducted with a PM fiber coil of 1.05 km length demonstrates that the method is effective in improving the spatial resolution and cross-talk measurement accuracy and can be readily incorporated in the analysis software. The described technology can be used in various applications, e.g., obtaining accurate polarization cross-talk measurements of PM fiber coils with lengths of longer than a few hundred meters and can be used to use the externally triggered crosstalk and the measurements of such crosstalk for various measurements and sensing applications FIG. 3 shows an example of a device for measuring a PM fiber coil. This device can function as a distributed polarization crosstalk analyzer. A polarized broadband light source 301 is coupled into one of the principal polarization axes of an optical birefringent medium 110. Such a polarized broadband light source 301 can be implemented in various configurations, such as a combination of a broadband light source and an optical polarizer. In the example in FIG. 3, the polarized broadband light source 301 is shown as a polarized super luminescent diode source (SLED) with a short coherence length. The polarized output light 101 is directed to be aligned with the slow axis of a PM fiber 110 at point A which is an input fiber connector for connecting the PM fiber coil 110. The PM fiber coil 110 terminates at the output connector C to output light to an optical linear polarizer 120 which is oriented at an angle with respect to the two principal polarization axes of the PM fiber coil 110, e.g., at 45 degrees. Referring to FIG. 1B, the polarizer 120 transmits part of the light output from the PM fiber coil 110 and mixes the two orthogonal polarizations together.

The PM fiber coil 110 is an optical birefringent medium that supports two orthogonal polarization modes along the PM fiber slow and fast principal axes and the input polarization of the light 101 is aligned with one of the principal polarization axes at the input point A, e.g., the slow axis. The optical output signal out of the optical birefringent medium 110 is directed the optical interferometer 230 to obtain optical interference of light between the two orthogonal polarization modes. The optical interferometer 230 produces an optical interference signal 312. A photodetector 150 is used to convert the signal 312 into a detector signal that carries the optical interference information. A data acquisition device or card (DAQ) 330 is used to covert the detector signal into data and a processor 340, e.g., a microprocessor or computer, is used to receive the data and processes the obtained optical interference to obtain an envelope spectral function of a polarization crosstalk between the two orthogonal polarization modes in the optical birefringent medium 110. Notably, the processor 340 is programmed to apply a compensation function based on measurements of the optical birefringent medium 110 to the envelope spectral function to reduce a spectral broadening in the envelope spectral function caused by optical birefringent dispersion in the optical birefringent medium 110.

The optical interferometer 230 in FIG. 3 is a fiber-based optical interferometer that includes a fiber coupler 310 with four fiber ports: port 1 as the interferometer input for receiving light from the polarizer 120, port 2 as the interferometer output port for sending out the signal 312, port 3 for connecting to a first optical path of the interferometer 230 and port 4 for connecting to a second optical path of the interferometer 230. The fiber coupler 310 splits the input light into a first beam to the port 3 and the first optical path and a second beam to the port 4 and the second optical path. The first optical path includes a fiber which terminates at a first Faraday mirror 321 which rotates polarization of light by 45 degrees in one pass and thus produces a 90-degree rotation in the polarization of the reflected light. Similarly, the second optical path includes a fiber which terminates at a second Faraday mirror 321 which produces a 90-degree rotation in the polarization of the reflected light. The reflected light beams from both the first and second optical paths are then mixed at the fiber coupler 310 to cause interference based on the optical path length difference between the first and second optical paths. This is a Michelson interferometer. A variable delay mechanism is provided to control the relative delay between the two paths. For example, a variable delay element 323 is placed in the first optical path in FIG. 3 to adjust and control the relative delay in response to a delay control signal 342 from the processor which further operates as a control device. In operation, the variable delay element 323 is scanned to operate the interferometer 230 as a scanning Michelson interferometer.

Consider an example in FIG. 3 where, at point B in the PM fiber coil 110, a polarization cross talk is induced by an external disturbance and some light is coupled from the initial input polarization at point A along the slow axis of the PM fiber coil 110 into the fast axis of the PM fiber 110 with a coupling coefficient parameter represented by the intensity or power ratio between the two polarizations $h=I_1/I_2$, where $I_1$ and $I_2$ are the powers in the fast and slow axes of the PM fiber 110, respectively. Because light polarized along the fast axis travels faster than that along the slow axis, at the output point C of the fiber 110, the faster component is ahead of the slow component by $\Delta nZ$, where $\Delta n$ is the group birefringence of the PM fiber 110 and Z is the fiber length between the crosstalk point B and the fiber end at point C. The polarizer 120 oriented at 45° to the slow axis placed at the output of the fiber projects both polarization components onto the same direction to cause interference between the two components in a scanning Michelson interferometer 230. When the relative optical path length is scanned, an interference peak appears when the polarization components overlap in space and disappears when they are separated more than the coherence length of the light source 301. The location B where the cross-talk occurs can be calculated from $z=\Delta z/\Delta n$ and cross-talk amplitude h can be obtained from the interference signal amplitude. FIG. 3 shows a train of the signals at three locations A, B and C in the PM fiber coil 110 illustrating polarization components along the slow axis and the fast axis.

The envelope of a measured cross-talk peak (the interference peak) is influenced by the spectral distribution of the light source 301 and the birefringence dispersion $\Delta D$ of the PM fiber 110. Assume that the SLED 301 has a Gaussian spectral shape, the cross-talk envelope (the degree of coherence) $\gamma$ can be derived as the function of birefringence dispersive $\Delta D$ and the distance Z of cross-talk point measured from the output:

$$|\gamma(Z, \Delta D)| = \frac{\sqrt{h-h^2}}{(1+\rho^2)^{1/4}} \exp\left\{-\left[\frac{2\delta d}{(1+\rho^2)^{1/2}W_0}\right]^2\right\} \quad (10)$$

where $$\delta d = (\Delta nZ - d) \quad (11)$$

$$\rho = 2\pi c(\Delta\lambda/\lambda_0)^2 \Delta DZ = \alpha\Delta DZ \quad (12)$$

$$\Delta D = d\tau/d\lambda = -[\omega^2/2\pi c](d^2\Delta\beta/d\omega^2)_0 \quad (13)$$

In the equations above, d is the path length imbalance of the scanned Michelson interferometer, $\rho$ is the accumulated birefringence dispersion along the fiber, c is the speed of light in free space, $\Delta\lambda$ and $\lambda_0$ are the spectral width and center wavelength of the light source, $\Delta\beta$ is the propagation constant difference of two polarization eigenmodes, $W_0$ is the 1/e width of the interference envelope when the dispersion $\rho$ is zero. This width is also the coherence length of the light source. Based on Eq. (11), the parameter $\delta d$ can be adjusted by varying the path length difference d of the delay line in the interferometer. The interference signal appears when the path length imbalance d compensates for optical path length difference $\Delta nZ$ between two polarization modes. Eq. (11) to Eq. (13) indicate that both the magnitude and the shape of the measured cross-talk envelope are functions of $\Delta D$ and Z. The degrading effects of birefringence dispersion $\Delta D$ on a cross-talk measurement are the reduction of the cross-talk envelope's amplitude and the broadening its shape as Z increases.

Notably, the effects of birefringence dispersion can be directly removed by multiplying the cross-talk measurement data with a dispersion compensation function $K(\rho)$:

$$K(\rho) = \sqrt[4]{1+\rho^2} \exp\left\{-\left[\frac{2\delta d\rho}{(1+\rho^2)^{1/2}W_0}\right]^2\right\} \quad (14)$$

Therefore, the original cross-talk envelope can be completely restored by simply multiply Eq. (14) with Eq. (10):

$$\gamma(Z, \Delta D) \cdot K(\rho) = \sqrt{h-h^2} \exp\left[-\left(\frac{2\delta d}{W_0}\right)^2\right] \quad (15)$$

In order to complete the compensation function, the birefringence dispersion $\Delta D$ or $\rho$ must be obtained first. From Eq. (10) one yields the relation between envelop broadening and birefringence dispersion as:

$$W/W_o = (1+\rho^2)^{1/2} = (1+(\alpha\Delta D)^2 Z^2)^{1/2} \quad (16)$$

Therefore, in principle the birefringence dispersion $\Delta D$ can be readily calculated by measuring the widths of cross-talk envelops at input (Z=L) and output (Z=0) ends of the PM fiber. In practice, in order to increase the accuracy of $\Delta D$, widths of cross-talk envelops at multiple locations along the PM fiber are measured and $\Delta D$ is obtained by curve-fitting to Eq. (16).

Figure 4:
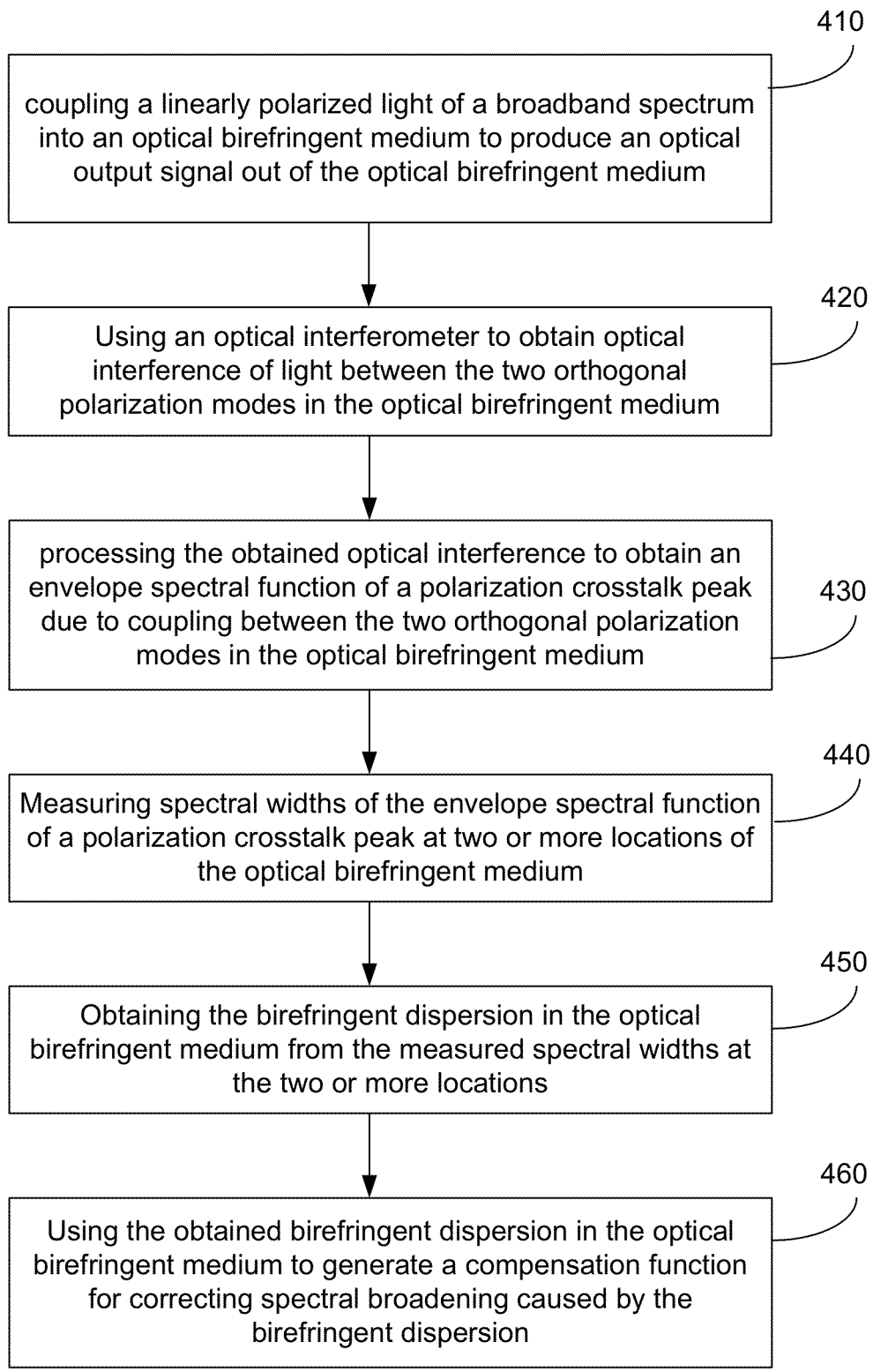
FIG. 4 shows an example of a process for obtaining the birefringent dispersion compensation function based on measuring spectral widths of the envelope spectral function of a polarization crosstalk peak at two or more locations of the optical birefringent medium.
Figure 5:
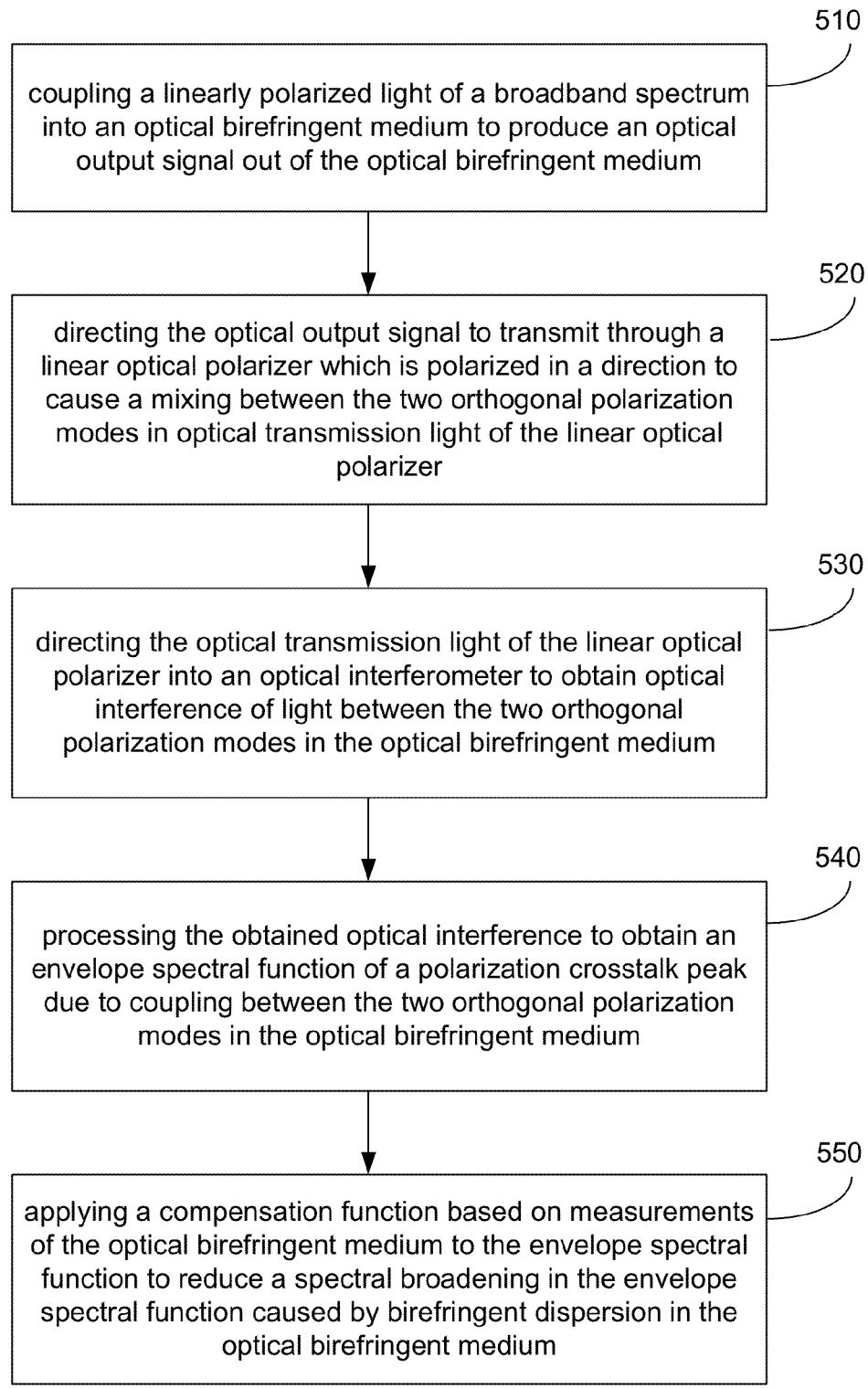
FIG. 5 shows an example of a process for measuring the polarization crosstalk in an optical birefringent medium such as PM fiber based on applying a birefringent dispersion compensation function.

FIGS. 4 and 5 illustrate operational processes of the device in FIG. 3.

FIG. 4 shows an example of a process for obtaining the birefringent dispersion compensation function based on measuring spectral widths of the envelope spectral function of a polarization crosstalk peak at two or more locations of the optical birefringent medium. At 410, a linearly polarized light of a broadband spectrum is coupled into the optical birefringent medium in a direction along which the optical birefringent medium supports two orthogonal polarization modes due to optical birefringence to produce an optical output signal out of the optical birefringent medium. At 420, the optical interferometer is used to process the optical output signal to obtain optical interference of light between the two orthogonal polarization modes in the optical birefringent medium. At 430, the obtained optical interference from the optical interferometer is processed to obtain an envelope spectral function of a polarization crosstalk peak due to coupling between the two orthogonal polarization modes in the optical birefringent medium. At 440, spectral widths of the envelope spectral function of a polarization crosstalk peak are measured at two or more locations of the optical birefringent medium, e.g., the input point A and output point B in FIG. 3. Step 450 is carried out to obtain the birefringent dispersion in the optical birefringent medium from the measured spectral widths at the two or more locations. At step 460, the obtained birefringent dispersion in the optical birefringent medium is used to generate the compensation function for correcting spectral broadening caused by the birefringent dispersion.

Based on the birefringent dispersion compensation function obtained in FIG. 4, FIG. 5 shows an example of a process for measuring the polarization crosstalk in an optical birefringent medium such as PM fiber based on applying the birefringent dispersion compensation function.

Figure 6:
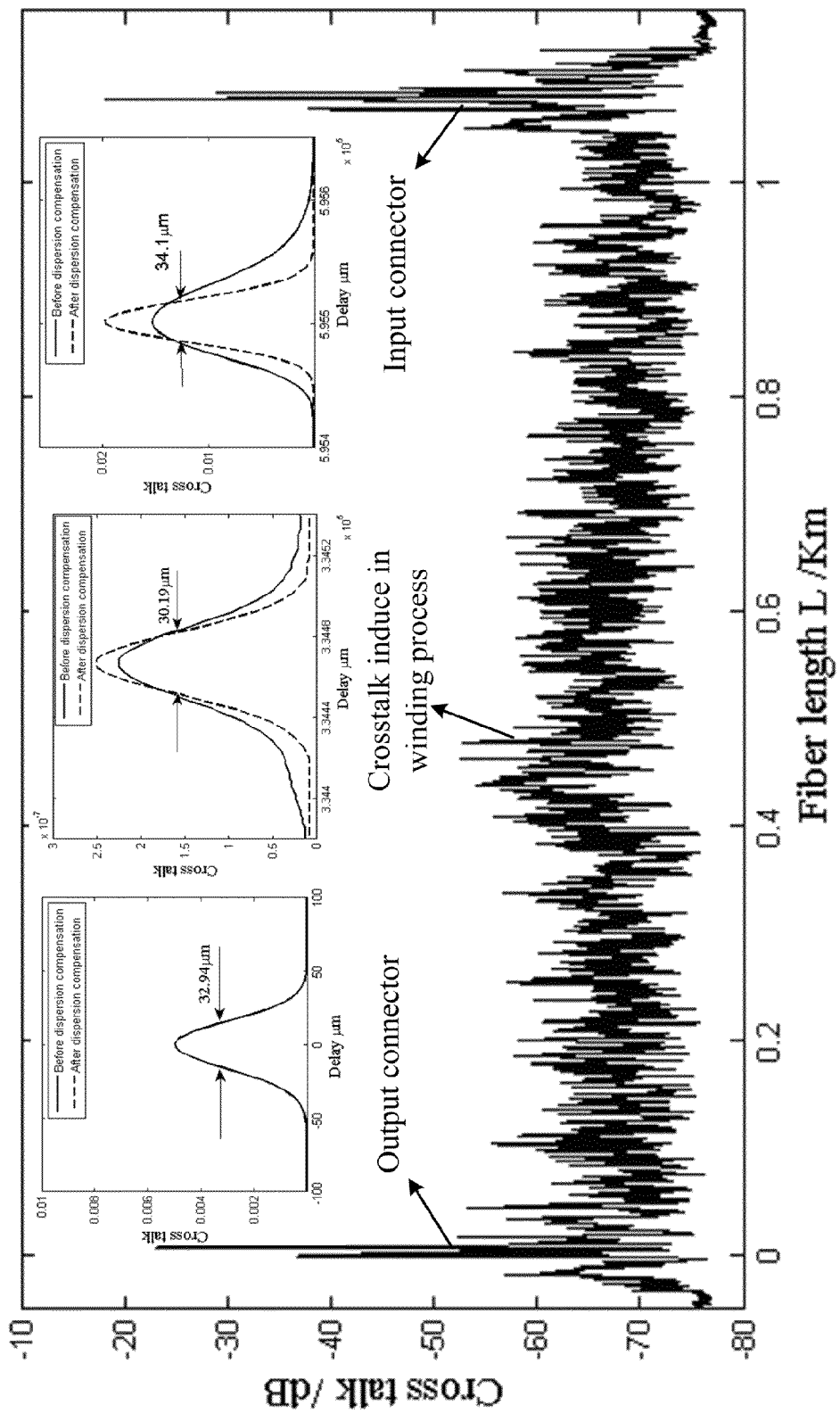
FIG. 6 shows an example of a polarization cross-talk curve of a PM fiber coil. The inserts show both the amplitude and width of cross-talk envelopes at output and input connectors, as well as in the middle region of the fiber before (solid line) and after (dotted line) birefringence dispersion compensation.

FIG. 6 is a measured polarization cross-talk curve of a PM fiber coil based on FIG. 3, showing the effects of birefringence dispersion on the measured cross-talk peaks and how the compensation removes those effects. The peaks at far left and far right correspond to cross-talks induced at output and input connectors A and C from slight fiber axis misalignment. The small peaks in between are the cross-talks induced by stresses during fiber winding process. The solid line in the right insert shows that birefringence dispersion causes two adverse effects: (1) broadening the envelop and (2) diminishing the amplitude of the cross-talk peak occurred at input connector A. The dotted line shows that both the envelop and the amplitude of the cross-talk peak are restored after dispersion compensation is performed. In particular, the envelope width of the peak at input connector is 34.1 μm after dispersion compensation, which is close to 32.4 μm of the left peak induced by the output connector C with zero dispersion (Z=0).

Figure 7A:
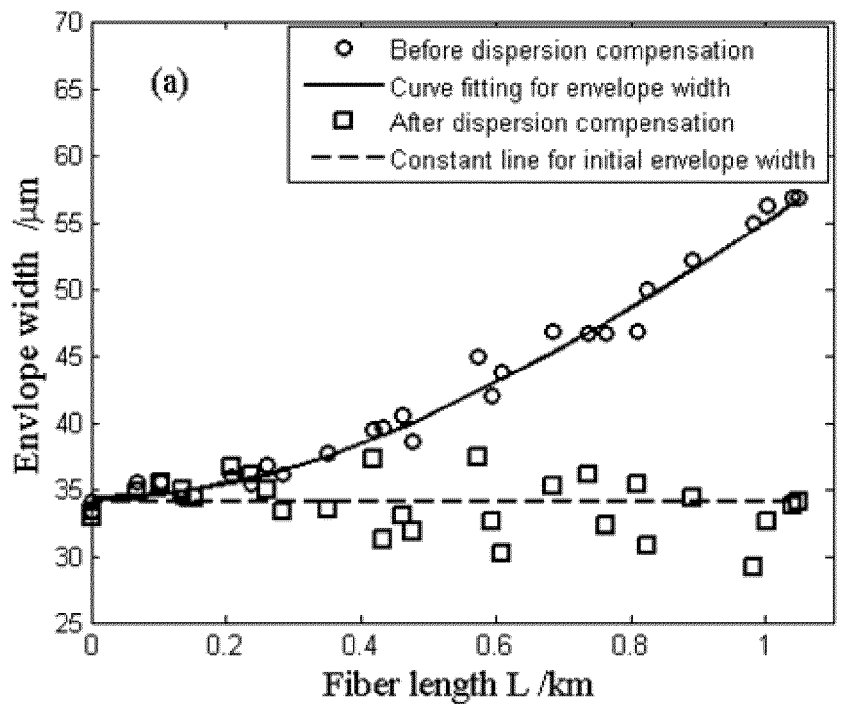
FIG. 7A shows exemplary measurements of the envelop widths of crosstalk peaks induced by stress at various locations PM fiber samples by using the system in FIG. 3.

FIG. 7A shows the measured envelope width as a function of the distance Z. in various tests conducted by using the system shown in FIG. 3. Measurements for multiple polarization cross-talks were performed at different locations along the PM fiber under test. The measurements clearly show that the width increases quadratically with distance Z due to the effect of birefringence dispersion. This behavior is in agreement with Eq. (16). Under the condition of the tests with the PM fiber used, such width broadening due to birefringence dispersion starts to degrade the spatial resolution of polarization cross-talk measurements for distance larger than about two hundred meters.

The birefringence dispersion ΔD of the PM fiber is then accurately obtained by the least-squares fitting the data to Eq. (16) to be 0.0014 ps/(km nm). Substituting the fitting obtained values of αΔD into Eq. (14), we complete the dispersion compensation function. Multiplication of the dispersion compensation function with the original measured crosstalk data produces a modified cross talk data where the dependence of polarization cross-talk on birefringence dispersion ΔD is cancelled.

Figure 7B:
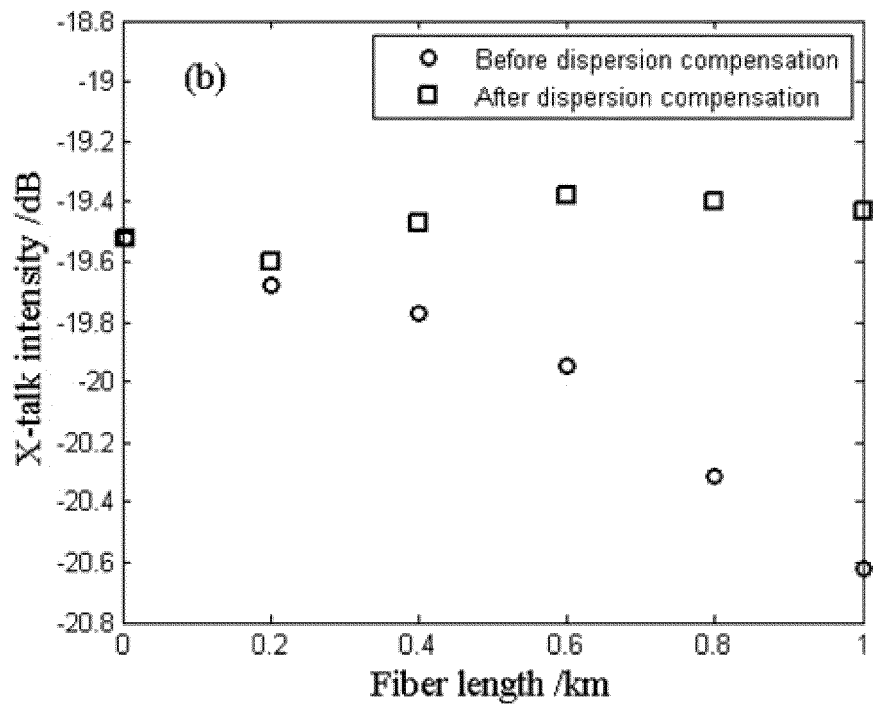
FIG. 7B shows exemplary measured values d crosstalk of the input connector with six different PM fiber lengths.

FIG. 7A shows an example of the envelop width of crosstalk peaks induced by stress at various locations along a PM fiber. The squares in FIG. 7A represent the envelope widths after the width broadenings of the cross-talk peaks are removed from the initial measured envelope widths represented by dots after the dispersion compensation is performed. FIG. 7B shows exemplary measured values d crosstalk of the input connector with six different PM fiber lengths (5 m, 205 m, 405 m, 605 m, 805 m and 1005 m). The crosstalk of the input connector is fixed and five segments of fibers with a length of 200 m each are sequentially spliced to the pigtail of the input connector for increased dispersion. The amplitude of polarization cross-talk decreases with the fiber length Z due to birefringence dispersion and is restored after performing the compensation.

Therefore, the dispersion compensation technique can effectively mitigate the cross-talk amplitude reduction and the line broadening caused by the dispersion. As such, the described compensation technique can effectively improve the spatial resolution and accuracy of cross-talk amplitude measurements using a broadband light source (e.g., a white-light) in an optical interferometer based polarization cross-talk analyzers.

While this document contains many specific implementation details, these should not be construed as limitations on the scope of the invention or of what may be claimed, but rather as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, the separation of various system components in the embodiments described above should not be understood as requiring such separation in all embodiments.

Thus, particular implementations are disclosed. Variations, modifications and enhancements of the disclosed implementations and other implementations can be made based on what is described and illustrated in this document.

What is claimed is:

1. A method for measuring polarization crosstalk in an optical birefringent medium, comprising:

coupling a linearly polarized light of a broadband spectrum into an optical birefringent medium that supports two orthogonal polarization modes due to optical birefringence to produce an optical output signal out of the optical birefringent medium, wherein the optical birefringent medium includes at least one location within the optical birefringent medium to cause a polarization crosstalk between the two orthogonal polarization modes in the optical birefringent medium;

directing the optical output signal into an optical interferometer to obtain optical interference of light between the two orthogonal polarization modes that includes location information on the location of the polarization crosstalk in the optical birefringent medium and a degree of the polarization crosstalk;

processing the obtained optical interference to obtain an envelope spectral function of the polarization crosstalk between the two orthogonal polarization modes in the optical birefringent medium to extract the location information of the polarization crosstalk in the optical birefringent medium and the degree of the polarization crosstalk; and applying a compensation function based on measurements of the optical birefringent medium to the envelope spectral function to reduce a spectral broadening in the envelope spectral function caused by optical birefringent dispersion due to presence of the two orthogonal polarization modes in the optical birefringent medium to restore an amplitude and a spectral width of a line shape of the envelope spectral function for improved accuracy in extracting the location information of the polarization crosstalk in the optical birefringent medium and the degree of the polarization crosstalk.

2. The method as in claim 1, comprising:

using spectral widths of the envelope spectral function measured at two or more different locations along the optical path in the optical birefringent medium to extract the optical birefringent dispersion of the optical birefringent medium; and using the obtained birefringent dispersion in the optical birefringent medium to generate the compensation function for correcting spectral broadening caused by the optical birefringent dispersion in the optical birefringent medium.

3. The method as in claim 2, comprising:

applying the compensation function based on measurements of the optical birefringent medium to the envelope spectral function includes multiplying the envelope spectral function by the compensation function to produce a modified envelope spectral function that has a spectral width with reduced spectral broadening caused by the optical birefringent dispersion.

4. The method as in claim 1, comprising:

using a fiber-based interferometer as the optical interferometer.

5. The method as in claim 1, comprising:

using a fiber-based device as the optical interferometer.

6. The method as in claim 1, wherein:

the optical interferometer is a Michelson interferometer.

7. The method as in claim 1, comprising:

using a length of polarization maintaining (PM) fiber as the optical birefringent medium.

8. The method as in claim 1, wherein the dispersion compensation function $K(\rho)$ is given by $$K(\rho) = \sqrt[4]{1+\rho^2} \exp\left\{-\left[\frac{2\delta d\rho}{(1+\rho^2)^{1/2} W_0}\right]^2\right\}$$

wherein $$\delta d = (\Delta n Z - d)$$

$$\rho = 2\pi c (\Delta\lambda/\lambda_0)^2 \Delta D Z = \alpha \Delta D Z$$

$$\Delta D = d\tau/d\lambda = -[\omega^2/2\pi c](d^2\Delta\beta/d\omega^2)_0$$

wherein, $\Delta D$ is the birefringence dispersion of the optical birefringent medium, $Z$ is a distance of the location of the polarization crosstalk in the optical birefringent medium from the optical interferometer, $d$ is a path length imbalance of two optical paths within the optical interferometer, $\rho$ is an accumulated birefringence dispersion along the optical birefringent medium, $c$ is speed of light in free space, $\Delta\lambda$ and $\lambda_0$ are a spectral width and a center wavelength of the light source, $\Delta\beta$ is a propagation constant difference of the two orthogonal polarization modes, $W_0$ is a 1/e width of an interference envelope when the dispersion $\rho$ is zero, $\Delta n$ is the difference of the refractive indices of the slow and fast axes, and $\omega$ is the angular frequency of the light.

9. A device for measuring polarization cross talk in an optical birefringent medium, comprising:

a mechanism that couples a linearly polarized light of a broadband spectrum into an optical birefringent medium that supports two orthogonal polarization modes due to optical birefringence and produces an optical output signal out of the optical birefringent medium, wherein the optical birefringent medium includes at least one location within the optical birefringent medium to cause a polarization crosstalk between the two orthogonal polarization modes in the optical birefringent medium;

an optical interferometer located to receive the optical output signal out of the optical birefringent medium and structured to obtain optical interference of light between the two orthogonal polarization modes in the optical birefringent medium that includes location information on the location of the polarization crosstalk in the optical birefringent medium and a degree of the polarization crosstalk; and a processing device that processes the obtained optical interference to obtain an envelope spectral function of the polarization crosstalk between the two orthogonal polarization modes in the optical birefringent medium to extract the location information of the polarization crosstalk in the optical birefringent medium and the degree of the polarization crosstalk and applies a compensation function based on measurements of the optical birefringent medium to the envelope spectral function to reduce a spectral broadening in the envelope spectral function caused by optical birefringent dispersion due to presence of the two orthogonal polarization modes in the optical birefringent medium to restore an amplitude and a spectral width of a line shape of the envelope spectral function for improved accuracy in extracting the location information of the polarization crosstalk in the optical birefringent medium and the degree of the polarization crosstalk.

10. The device as in claim 9, wherein:

the processing device is configured to use values of spectral widths of the envelope spectral function measured at two or more different locations along the optical path in the optical birefringent medium as the measurements of the optical birefringent medium for the compensation function.

11. The device as in claim 9, wherein:
the processing device is configured to apply the compensation function to the envelope spectral function by multiplying the envelope spectral function by the compensation function to produce a modified envelope spectral function that has a spectral width with reduced spectral broadening caused by the optical birefringent dispersion.

12. The device as in claim 9, wherein:
the optical interferometer is a fiber-based interferometer.

13. The device as in claim 9, wherein:
the optical interferometer is a Michelson interferometer.

14. The device as in claim 9, comprising:
a linear optical polarizer which is polarized in a direction to cause a mixing between the two orthogonal polarization modes in the optical output signal from the optical birefringent medium and is located upstream to the optical interferometer so that the optical output signal out of the linear optical polarizer is directed into the optical interferometer, and
wherein the optical interferometer includes
a fiber coupler that receives the optical output signal out of the linear optical polarizer to split the received light into first and second optical beams,
a first fiber line coupled to the fiber coupler to receive the first optical beam,
a first Faraday mirror coupled to the first fiber line to reflect light back to the first fiber line;
a second fiber line coupled to the fiber coupler to receive the second optical beam;
a second Faraday mirror coupled to the second fiber line to reflect light back to the second fiber line, wherein the fiber coupler receives reflected light from both the first and second fiber lines to cause the optical interference;
a variable optical delay element coupled in the second fiber line to adjust a delay in the second fiber line; and
a photodetector that detects an output of the fiber coupler carrying the optical interference and outputs an electrical signal carrying the optical interference to be processed by the processing device.

15. The device as in claim 9, wherein the dispersion compensation function $K(\rho)$ is given by $$K(\rho) = \sqrt[4]{1+\rho^2}\exp\left\{-\left[\frac{2\delta d\rho}{(1+\rho^2)^{1/2}W_0}\right]^2\right\}$$

wherein $\delta d = (\Delta n Z - d)$ $\rho = 2\pi c(\Delta\lambda/\lambda_0)^2 \Delta DZ = \alpha\Delta DZ$ $\Delta D = d\tau/d\lambda = -[\omega^2/2\pi c](d^2\Delta\beta/d\omega^2)_0$ wherein, $\Delta D$ is the birefringence dispersion of the optical birefringent medium, Z is a distance of the location of the polarization crosstalk in the optical birefringent medium from the optical interferometer, d is a path length imbalance of two optical paths within the optical interferometer, $\rho$ is an accumulated birefringence dispersion along the optical birefringent medium, c is speed of light in free space, $\Delta\lambda$ and $\lambda_0$ are a spectral width and a center wavelength of the light source, $\Delta\beta$ is a propagation constant difference of the two orthogonal polarization modes, $W_0$ is a 1/e width of an interference envelope when the dispersion $\rho$ is zero, $\Delta n$ is the difference of the refractive indices of the slow and fast axes, and $\omega$ is the angular frequency of the light.

16. A device for measuring polarization crosstalk in an optical birefringent medium, comprising:
a broadband light source module that produces a linearly polarized light of a broadband spectrum into an optical birefringent medium that supports two orthogonal polarization modes due to optical birefringence to produce an optical output signal out of the optical birefringent medium, wherein the optical birefringent medium includes at least one location within the optical birefringent medium to cause a polarization crosstalk between the two orthogonal polarization modes in the optical birefringent medium;
an optical interferometer that receives the optical output signal out of the optical birefringent medium to obtain optical interference of light between the two orthogonal polarization modes that includes location information on the location of the polarization crosstalk in the optical birefringent medium and a degree of the polarization crosstalk;
an optical detector that receives an optical output from the optical interferometer carrying the optical interference and produces a detector output; and
a processor that processes the detector output to obtain an envelope spectral function of the polarization crosstalk between the two orthogonal polarization modes in the optical birefringent medium to extract the location information of the polarization crosstalk in the optical birefringent medium and the degree of the polarization crosstalk, the processor outputting a control signal to the optical interferometer to control a relative delay between two optical paths in the optical interferometer for obtaining the envelope spectral function and applying a compensation function based on measurements of the optical birefringent medium to the envelope spectral function to reduce a spectral broadening in the envelope spectral function caused by optical birefringent dispersion due to presence of the two orthogonal polarization modes in the optical birefringent medium to restore an amplitude and a spectral width of a line shape of the envelope spectral function for improved accuracy in extracting the location information of the polarization crosstalk in the optical birefringent medium and the degree of the polarization crosstalk.

17. The device as in claim 16, wherein:
the processing device is configured to apply the compensation function to the envelope spectral function by multiplying the envelope spectral function by the compensation function to produce a modified envelope spectral function that has a spectral width with reduced spectral broadening caused by the optical birefringent dispersion.

18. The device as in claim 16, wherein the dispersion compensation function $K(\rho)$ is given by $$K(\rho) = \sqrt[4]{1+\rho^2}\exp\left\{-\left[\frac{2\delta d\rho}{(1+\rho^2)^{1/2}W_0}\right]^2\right\}$$

wherein $\delta d = (\Delta n Z - d)$ $\rho = 2\pi c(\Delta\lambda/\lambda_0)^2 \Delta DZ = \alpha\Delta DZ$ $\Delta D = d\tau/d\lambda = -[\omega^2/2\pi c](d^2\Delta\beta/d\omega^2)_0$ wherein, $\Delta D$ is the birefringence dispersion of the optical birefringent medium, Z is a distance of the location of the polarization crosstalk in the optical birefringent medium from the optical interferometer, d is a path length imbalance of two optical paths within the optical interferometer, $\rho$ is an accumulated birefringence dispersion along the optical birefringent medium, c is speed of light in free space, $\Delta\lambda$ and $\lambda_0$ are a spectral width and a center wavelength of the light source, $\Delta\beta$ is a propagation constant difference of the two orthogonal polarization modes, $W_0$ is a 1/e width of an interference envelope when the dispersion $\rho$ is zero, $\Delta n$ is the difference of the refractive indices of the slow and fast axes, and $\omega$ is the angular frequency of the light.

\* \* \* \* \*